United States Patent
Pensel et al.

(10) Patent No.: US 6,377,397 B1
(45) Date of Patent: Apr. 23, 2002

(54) ILLUMINATION DEVICE FOR A SURGICAL MICROSCOPE

(75) Inventors: Juergen Pensel, Altstätten; Ulrich Sander, Rebstein, both of (CH)

(73) Assignee: Leica Microsystems AG, Heerbrugg (CH)

( * ) Notice: Subject to any disclaimer, the term of this patent is extended or adjusted under 35 U.S.C. 154(b) by 0 days.

(21) Appl. No.: 09/656,902

(22) Filed: Sep. 7, 2000

(30) Foreign Application Priority Data

Sep. 9, 1999 (CH) .............................. 1651/99

(51) Int. Cl.⁷ .............................. G02B 21/06; G02B 5/04
(52) U.S. Cl. ..................... 359/389; 359/385; 359/831
(58) Field of Search ................. 359/368–390, 359/738–739, 885–892

(56) References Cited

U.S. PATENT DOCUMENTS

| | | | |
|---|---|---|---|
| 3,843,235 A | * 10/1974 | Mino et al. ................. | 359/888 |
| 4,127,318 A | * 11/1978 | Determann et al. .......... | 359/387 |
| 4,165,180 A | * 8/1979 | Failes .......................... | 356/310 |
| 5,099,131 A | * 3/1992 | Brownrigg et al. ....... | 250/458.1 |
| 5,126,877 A | 6/1992 | Biber .......................... | 359/389 |
| 5,706,091 A | * 1/1998 | Shiraishi ..................... | 356/399 |

OTHER PUBLICATIONS

Wild Heerbrugg AG, Product Brochure M1 668d–X.85, Oct. 1985, republished by successor Leica Microsystems Ltd., Business Unit SOM, as Product Brochure Publication No. 10 M1 668 Oen —"Photography and Video Dual Attachment for Leica Surgical Microscopes."

English Abstract of Japanese application serial No. 9–105866.

* cited by examiner

*Primary Examiner*—Thong Nguyen
(74) *Attorney, Agent, or Firm*—Hodgson Russ LLP

(57) ABSTRACT

The invention concerns an illumination device having a stop (8) for a surgical microscope, whose stop (8) is capable of covering a partial light flux of the illumination system, the coverage not being accomplished completely as a result of the particular configuration of the stop.

12 Claims, 2 Drawing Sheets

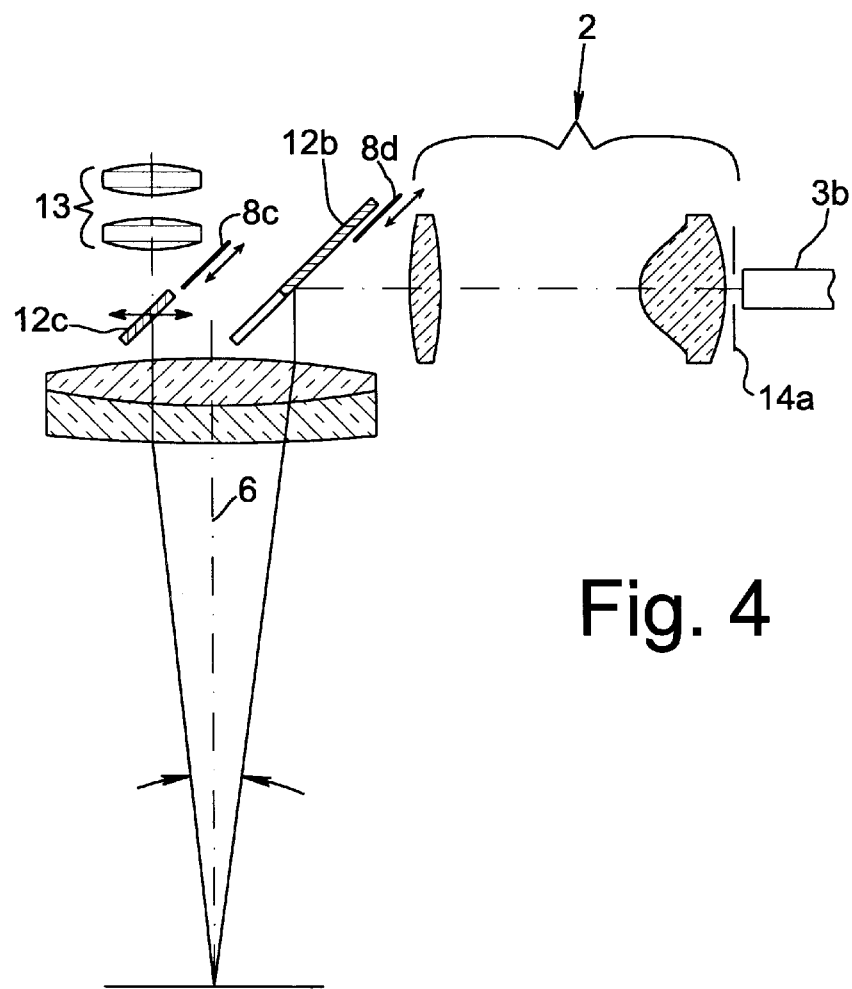
Fig. 4
Fig. 5
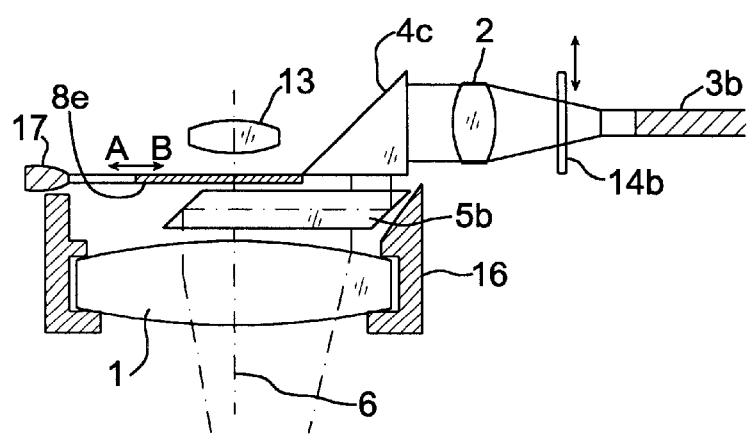

ILLUMINATION DEVICE FOR A SURGICAL MICROSCOPE

CROSS REFERENCE TO RELATED APPLICATIONS

This invention claims priority of a Swiss filed patent application CH P 1651/99 filed Sep. 9, 1999.

FIELD OF THE INVENTION

The invention concerns devices for illuminating a surgical field of view of a surgical microscope, for example an ophthalmic surgical microscope.

BACKGROUND OF THE INVENTION

It is known to provide an illumination device for a surgical microscope in which the entire light beam from an illumination optical system associated with a lamp is deflected by a first prism out of a perpendicular to the principal axis of the principal objective of the microscope into an oblique inclination at a small angle with respect to the principal axis, and in which a second portion of the total light beam quantity is cast onto the surgical field approximately parallel to the principal axis. This configuration is used in particular for ophthalmic surgery. In the center of the surgical field, the illumination is approximately parallel to the surgical microscope axis, whereas around that center it radiates at a small angle toward the surgical field. During the surgery, the illumination component at a small angle is usually blocked out by a slide-in stop, so that the surgeon has available only the parallel illumination component. As a result, however, the actual illuminated surgical field is also narrowed down to the diameter of the illumination with the parallel component.

This has in some cases been perceived as a disadvantage in practical use, so that the object of the invention is to achieve an improved blocking-out effect that nevertheless also admits some light for the region at a small angle, so that this region is not completely darkened.

One obvious step toward achieving this is not to place the stop, which is already provided as standard equipment, entirely in front of the prism output, but rather to leave open a small gap for a small amount of light to pass; with some equipment this is in fact done by users. Experiments have revealed, however, that this approach is not satisfactory because it causes severe distortion, vignetting, and illuminated areas with inhomogeneous brightness values distributed over the illumination field.

DE 40 28 605 C2 and its family member U.S. Pat. No. 5,126,877 present a known illumination device. An even earlier illumination device, functioning well per se, was already being commercialized in 1985 by the Applicant's predecessor under the name "0° illumination optical system" (cf. brochure M1 668d-X.85, October 1985, of Wild Heerbrugg AG). In the "0° illumination optical system," it is possible, by rotating a disk, to add selectably, to a standard illumination at a small angle to the principal axis, a "0° illumination" which reduces the light flux of the standard illumination in proportion to its own increase in light flux. Theoretically, it is possible in this context to control the light flux distribution.

Although this known configuration is well-established, a great deal of effort was nevertheless devoted to finding newer approaches that did not involve light flux distribution, i.e. in which quantities of light flux are not subtracted from the one type of light flux in favor of the other light flux type. One such approach is recited in the German and U.S. documents referenced above.

A much more recent known configuration is described in JP-A-9-105866. Somewhat comparable to the early "0° illumination" configuration of the Applicant's predecessor, here there is located under a first prism a second prism that has two mirror surfaces but is not rotatable about the principal axis. This configuration results in a fundamentally constant light flux distribution between the 0° light flux portion and the greater light flux component that is always incident at a small angle; an overall reduction in light flux is possible by way of a slide-in stop in the principal beam path of the illumination optical system.

BRIEF SUMMARY OF THE INVENTION

The problems of the prior art, including severe distortion, vignetting, and illuminated areas with inhomogeneous brightness values distributed over the illumination field, are eliminated by the invention by the fact that now, instead of an opaque stop, a stop with low light transmittance is used. A stop of this kind can be a neutral color filter, an aperture stop, a grid stop, or the like. According to a development of this invention, the light-transmitting areas of the stops could also be equipped with optical elements, thus resulting in a scattering of the light that, if necessary, illuminates the surgical field even beyond the illuminated area that has hitherto been standard. Instead of or in addition to such optical elements, markings such as, for example, crosshairs or the like could also be imaged in the illuminated field.

The user is thus given not only good perception of the surgical field but also, albeit only faintly, a view of, for example, surgical instruments introduced from the side and/or an additional indication concerning markings.

The stop can be arranged in front of either the light entry surfaces or the light exit surfaces of the light distribution and deflection apparatus.

The invention is not limited to these stops as recited, however, but rather can be equipped with any known or novel light regulation apparatus without losing its essence, namely the partially darkening configuration of the light beam at a small angle.

A particular embodiment and optionally an alternative to that described earlier, which can advantageously be utilized alternatively or also in combination and if necessary moreover results in an improved and even more symmetrical illumination, is characterized in that the stop is configured as a partially transparent mirror surface that deflects some of the beams emerging from the light distribution and deflection apparatus back toward the light source. With this configuration, when the one region is darkened, light can additionally be made available for the other, with no change in the output of the light source.

Independently of or in addition to the light flux control system, according to the present invention a light color control system can also be provided, such as color selection filter.

BRIEF DESCRIPTION OF THE DRAWINGS

The invention will be explained in more detail, by way of examples, with reference to the drawings, in which:

FIG. 4 shows a variant with mirrors instead of prisms, in which the novel stops according to the present invention can be slid in, alternatively or simultaneously, in front of both entry surfaces of the light distribution and deflection apparatus; and FIG. 5 shows a variant that is most similar to the earlier 0° illumination system of the Applicant, but has also been equipped with a new stop.

The Figures are described in linked fashion. Identical reference characters denote identical components. Identical reference characters with different indices denote parts with identical purposes or similar functions.

DETAILED DESCRIPTION OF THE INVENTION

Figure 1:
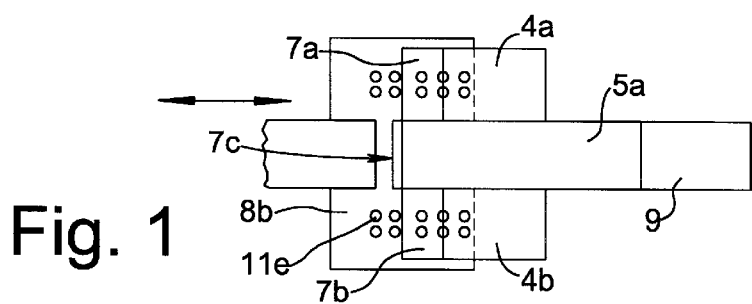
FIG. 1 shows a plan view of essential elements of a variant of the invention.

In the Figures, reference numeral 1 identifies a principal objective of a surgical microscope, and reference numeral 6 identifies a principal axis of objective 1.

Figure 2:
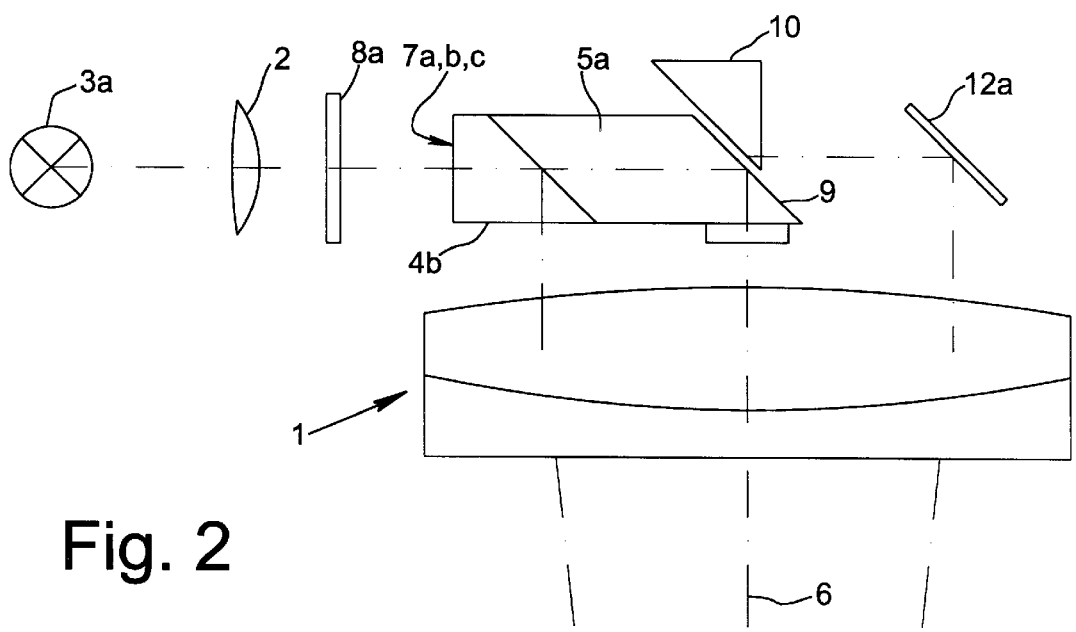
FIG. 2 shows an expanded side view of another variant, with a schematic illumination optical system and a principal objective.
Figure 3:
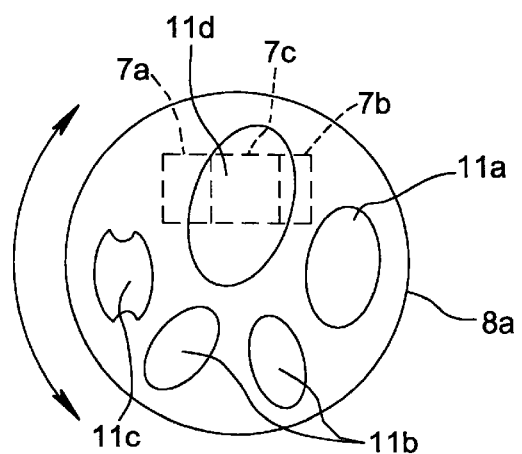
FIG. 3 shows an example of a stop disk according to the present invention.

In FIGS. 1 through 3, a two-part first prism 4a and 4b flanks a second prism 5a. The prisms are, for example, cemented to one another, but are isolated in light-tight fashion from one another. All the prisms each have one light entry surface 7 that faces toward an illumination optical system 2. Depicted by way of example is a light source 3a that could certainly also comprise a fiber optic cable (3b in FIGS. 4 and 5). The two-part nature of prism 4 is not obligatory but is preferred because it results in good symmetry in the illumination of the specimen. The arrangement could also be asymmetrical.

Optionally arranged between illumination optical system 2 and light entry surfaces 7 is an adjustable stop 8a. The appearance of this can be, for example, as depicted in FIG. 3, which shows windows 11a–11d that can be selectably placed in front of light entry surfaces 7. In FIG. 3, window 11d is located in front of light entry surface 7c of the second prism, so that in this case only the 0° illumination is activated at full light intensity. The two first prism parts 4a and 4b receive practically no light flux. If window 11d were to be rotated somewhat farther, it would thereby be possible to achieve a division of the light flux between light entry surface 7c and one of the two light entry surfaces 7a or 7b.

Provided as a very obvious alternative are windows 11b, which allow complete darkening of the 0° illumination while at the same time completely illuminating first prism 4a, 4b. Windows 11a allow complete illumination of all the prisms 4a, 4b, and 5a, and window 11c makes possible complete illumination of prism 5a with a simultaneous reduction in the illumination of first prism 4a, b.

Prisms 4a, b could also be configured in continuously integral fashion, so that the entire entry surface 7a, b, c is covered by prism 4. Prism 5a would then be cemented, as a narrower prism, onto the hypotenuse of prism 4. Of course prisms 4a, b and 5a could also be configured together as one integral prism.

Independently of stop 8a, a displaceable prism is optionally provided as refractive element 10 which is displaceable with a plane surface on total reflection surface 9 of second prism 5a. In a manner not depicted in detail, it rests, for example, in spring-loaded fashion against surface 9. As a result of the interruption in total reflection, a portion of the light flux out of second prism 5a is not reflected through principal objective 1, but rather is diverted through refractive element 10 out of second prism 5a.

A liquid film, for example an oil film, could be present here on the contact surface by way of assistance. In a variant that is not shown, this could result in light annihilation, for example if the surface of refractive element 10 on the right in the Figure is black, or if that surface is transparent but is directed toward a black inner tube coating.

In the context of the invention, total reflection can also be abolished by way of electro-optical layers (e.g. LCD, crystal, or vacuum-deposited layers) between the two prisms 4 and 5. If they are electronically excited, these layers can be selectively excited in order thereby to make the desired regions totally reflective or reflection-suppressing.

In the present exemplary embodiment, however, this surface is directed toward a further mirror surface 12a which in turn directs the deflected light flux, at a small angle or parallel depending on the mirror setting, through principal objective 1 toward the specimen. If necessary, the further mirror surface could also be adjustable in order to influence the angle of reflection, although this is not depicted in detail.

Stop 8b that can be slid in front of the light exit surfaces covers only a portion of the light flux. It is equipped with orifices 11e that allow a small amount of light to pass through. Instead of the orifices, diffusion lenses or the like can also be arranged for better light distribution.

Filter, grids (including metal and plastic grids), metallized glass plates, plastic plates, films, or the like can be used instead of stop 8a or perforated stop 8b that are depicted. Alternatively the stop 8b can be configured as a partially transparent mirror surface that deflects some of the beams emerging from the light distribution and deflection apparatus 10 back toward the light source 3a.

In a manner comparable to the stops 8a and 8b, a selective color selection filter is additionally or alternatively provided.

FIG. 4 depicts the light distribution and deflection element made up of mirrors 12b and 12c. Also indicated is an optical system 13 of the microscope beam path. Stops 8c and 8d can be adjusted independently of one another, and are configured like the variants described above. This principle is encompassed by the invention even if only one mirror can be covered by a novel stop 8d or 8c according to the present invention. Illumination optical system 2 is depicted symbolically in FIG. 4 with two lenses, preceding which is a stop 14a. Stops of this kind are provided as standard equipment in many units, and serve to delimit edges and/or to darken the overall illumination light. Selective darkening is not possible with them. A comparable stop 14b is shown in FIG. 5. In FIG. 5, displaceable stop 8e is configured in accordance with the invention, and thus allows selective but not complete darkening of the illumination at a small angle. Stop 8e is operable by way of a slider 17 that can be actuated in manual or motorized fashion. A mount 16 for principal objective 1, a prism 4c, and a parallelogram prism 5b are also depicted.

What is claimed is:

1. An illumination device on a surgical microscope having a principal objective on a principal axis and an illumination optical system and a light source, there being provided between the principal objective and the illumination optical system a light distribution and deflection apparatus with which, in an operating state, deflection of one portion of a light flux of the illumination optical system at a small angle to the principal axis, and another portion of the light flux of the illumination optical system parallel to the principal axis is effected, such that a portion of the light distribution and deflection apparatus can be covered by a stop, wherein the stop is not completely opaque.

2. The illumination device as defined in claim 1, wherein the stop is configured as a neutral-color light filter.

3. The illumination device as defined in claim 1, wherein the stop is arranged or is slidable between the illumination optical system and at least one entry surface of the light distribution and deflection apparatus.

4. The illumination device as defined in claim 3, wherein the light distribution and deflection apparatus comprises a plurality of light entry surfaces and the stop is configured as an inherently opaque disk having selectively advanceable light openings which, in accordance with requirements, give the illumination optical system beam access, to a varying extent, to the plurality of light entry surfaces into the light distribution and deflection apparatus.

5. The illumination device as defined in claim 1, wherein the light distribution and deflection apparatus comprises a plurality of light entry surfaces and the stop is configured as a liquid crystal element that, in electronically activated fashion, exposes unrestrictedly selectable portions of the plurality of light entry surfaces.

6. The illumination device as defined in claim 1, wherein the stop is configured as a perforated panel or perforated film.

7. The illumination device as defined in claim 6, wherein the stop is configured as a metallized glass or plastic plate.

8. The illumination device as defined in claim 7, wherein the stop is configured as a partially transparent mirror surface that deflects some light beams emerging from the light distribution and deflection apparatus back toward the light source.

9. The illumination device as defined in claim 1, wherein the stop is configured as a metal or plastic grid.

10. The illumination device as defined in claim 1, wherein the stop comprises a selective color selection filter.

11. The illumination device as defined in claim 1, wherein the stop carries, at light-transmissive points, optical elements to influence a partial illumination beam passing through it.

12. An illumination device on a surgical microscope having a principal objective about a principal axis and an illumination optical system and a light source, wherein there is provided between the principal objective and the illumination optical system a light distribution and deflection apparatus which, in an operating state, effects deflection of one portion of a light flux of the illumination optical system at a small angle to the principal axis, and deflection of another portion of the light flux of the illumination optical system parallel to the principal axis, the light distribution and deflection apparatus being arranged so that with its light entry surface it faces toward the illumination optical system in such a way that at least a partial light flux through the light distribution and deflection apparatus is controllable independently of the other partial light flux, and that there is provided for control purposes a stop that cannot completely cover the partial light flux in question.

\* \* \* \* \*